United States Patent [19]

Naito et al.

[11] Patent Number: 4,691,014
[45] Date of Patent: Sep. 1, 1987

[54] CEPHALOSPORIN COMPOUNDS

[75] Inventors: Takanobu Naito, Funabashi; Masaaki Yokoyama, Tokyo; Kazuya Sasaki, Higashikurume; Makoto Yamamoto, Tokyo; Kouji Amemiya, Kodaira, all of Japan

[73] Assignee: Kaken Pharmaceutical Co., Ltd., Tokyo, Japan

[21] Appl. No.: 782,567

[22] Filed: Oct. 1, 1985

[30] Foreign Application Priority Data

Oct. 19, 1984 [JP] Japan ................. 59-218660

[51] Int. Cl.$^4$ .................. C07D 501/22; A61K 31/545
[52] U.S. Cl. ..................... 540/227; 540/222; 540/225; 540/226; 540/228
[58] Field of Search ............... 540/227, 226, 228, 222, 540/225; 514/206, 203, 204

[56] References Cited

U.S. PATENT DOCUMENTS 4,603,129 7/1986 Blumbach et al. ................. 514/206

FOREIGN PATENT DOCUMENTS 58008087 7/1981 Japan .
5867697 9/1981 Japan .
59020288 7/1982 Japan .

*Primary Examiner*—Nicholas S. Rizzo
*Attorney, Agent, or Firm*—Oblon, Fisher, Spivak, McClelland, & Maier

[57] ABSTRACT

A cephalosporin compound having the formula:

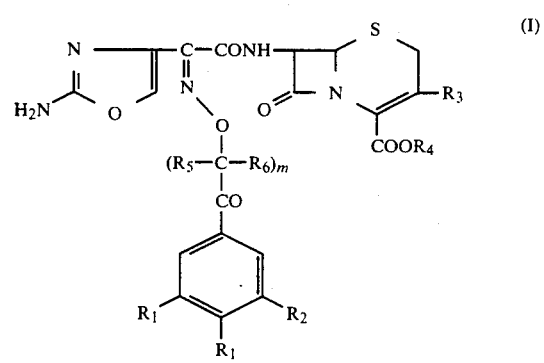

wherein $R_1$ is a hydroxy group, a lower alkanoyloxy group or a lower alkoxycarbonyloxy group, $R_2$ is a hydrogen atom, a hydroxy group, a lower alkanoyloxy group or a lower alkoxycarbonyloxy group, $R_3$ is a hydrogen atom, a halogen atom, a lower alkyl group, a lower alkenyl group, a lower alkoxy group or —$CH_2R_7$ (wherein $R_7$ is a hydrogen atom, an azido group, a lower alkanoyloxy group, a carbamoyloxy group, a substituted or unsubstituted pyridinium group or a substituted or unsubstituted heterocyclic thio group), $R_4$ is a hydrogen atom or a carboxy-protecting group, each of $R_5$ and $R_6$ is a hydrogen atom or a lower alkyl group, or $R_5$ and $R_6$ form a cycloalkylidene group together with the carbon atom to which they are attached, and m is 0 to 1, or a pharmaceutically acceptable salt thereof.

10 Claims, No Drawings

CEPHALOSPORIN COMPOUNDS

The present invention relates to novel cephalosporin compounds and their salts, and a process for their preparation.

More particularly, the present invention provides novel cephalosporin compounds represented by the formula:

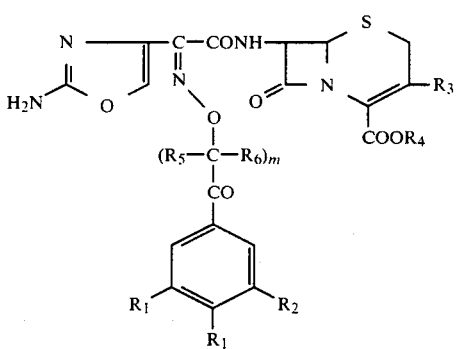

wherein $R_1$ is a hydroxy group, a lower alkanoyloxy group or a lower alkoxycarbonyloxy group, $R_2$ is a hydrogen atom, a hydroxy group, a lower alkanoyloxy group or a lower alkoxycarbonyloxy group, $R_3$ is a hydrogen atom, a halogen atom, a lower alkyl group, a lower alkenyl group, a lower alkoxy group or —$CH_2R_7$ (wherein $R_7$ is a hydrogen atom, an azido group, a lower alkanoyloxy group, a carbamoyloxy group, a substituted or unsubstituted pyridinium group or a substituted or unsubstituted heterocyclic thio group), $R_4$ is a hydrogen atom or a carboxy-protecting group, each of $R_5$ and $R_6$ is a hydrogen atom or a lower alkyl group, or $R_5$ and $R_6$ form a cycloalkylidene group together with the carbon atom to which they are attached, and m is 0 or 1, or a pharmaceutically acceptable salt thereof.

The present inventors have found that the cephalosporin compounds of the formula I have a wide range of antibiotic activities against not only gram-positive bacteria but also gram-negative bacteria including Pseudomonas aeruginosa. The present invention is based on this discovery.

Now, the present invention will be described in further detail with reference to the preferred embodiments.

Referring to $R_1$ in the formula I, the lower alkanoyloxy group represents, for instance, an acetoxy group, a propionyloxy group or a pivaloyloxy group; and the lower alkoxycarbonyloxy group represents, for instance, a methoxycarbonyloxy group, an ethoxycarbonyloxy group or a t-butoxycarbonyloxy group. Referring to $R_2$, the lower alkanoyloxy group represents, for instance, an acetoxy group, a propionyloxy group or a pivaloyloxy group; and the lower alkoxycarbonyloxy group represents, for instance, a methoxycarbonyloxy group, an ethoxycarbonyloxy group or a t-butoxycarbonyloxy group. Referring to $R_3$, the halogen atom represents, for instance, fluorine or chlorine; the lower alkyl group represents, for instance, a methyl group or an ethyl group; the lower alkenyl group represents, for instance, a vinyl group; and the lower alkoxy group represents, for instance, a methoxy group or an ethoxy group. Referring to $R_7$, the lower alkanoyloxy group represents, for instance, an acetoxy group; the substituted or unsubstituted pyridinium group represents, for instance, a 4-sulfoethyl pyridinium group; and the substituted or unsubstituted heterocyclic thio group represents, for instance, a 1-methyl-1H-tetrazol-5-yl-thio group, a 1-(2-N,N-dimethylamino)ethyl-1H-tetrazol-5-yl-thio group, a 1-carboxymethyl-1H-tetrazol-5-yl-thio group, a 2-methyl-1,3,4-thiadiazol-5-yl-thio group or a 2,5-dihydro-6-hydroxy-2-methyl-5-oxo-as-triazine-3-yl-thio group. Referring to $R_4$, the carboxy-protecting group represents, for instance, a group which is chemically readily removable, such as a t-butyl group, a benzhydryl group, a p-methoxybenzyl group, a t-butyldimethylsilyl group, a trimethylsilyl group or a p-nitrobenzyl group, or a group which can readily be decomposed under a biological condition, such as a pivaloyloxymethyl group or an acetoxymethyl group. Referring to $R_5$ and $R_6$, the lower alkyl group represents, for instance, a methyl group or an ethyl group; and the cycloalkylidene group formed by $R_5$ and $R_6$ together with the carbon atom to which they are attached, represents, for instance, a cyclopropylidene group.

$R_2$ is preferably a hydrogen atom or a lower alkanoyloxy group; $R_3$ is preferably —$CH_2R_7$ wherein $R_7$ is a lower alkanoyloxy group or a substituted or unsubstituted heterocyclic thio group; and each of $R_5$ and $R_6$ is preferably a hydrogen atom. Likewise, m is preferably 0.

As the pharmaceutically acceptable salts of the cephalosporin compounds of the formula I of the present invention, there may be mentioned an alkali metal salt such as a sodium or potassium salt, an alkaline earth metal salt such as a calcium or magnesium salt, a salt with an inorganic base such as an ammonium salt, a salt with an organic amine such as trimethylamine, triethylamine, diethanolamine or triethanolamine, a salt with a mineral acid such as hydrochloric acid or sulfuric acid, a salt with an organic carboxylic acid such as oxalic acid, formic acid, trichloroacetic acid or trifluoroacetic acid, and a salt with an organic sulfonic acid such as methanesulfonic acid or toluenesulfonic acid.

The cephalosporin compounds of the formula I may be prepared by the following method A or B.

Process A

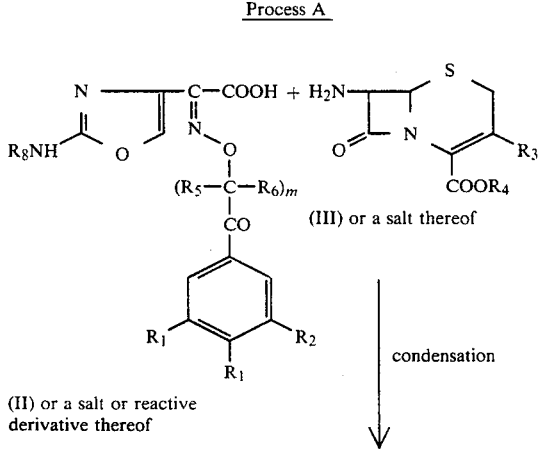

(II) or a salt or reactive derivative thereof

-continued
Process A

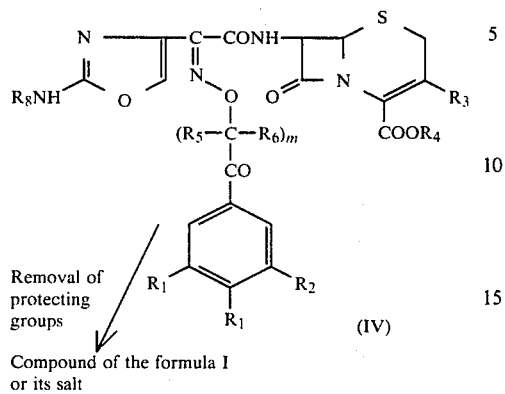

Compound of the formula I
or its salt

In the above formulas, $R_1$, $R_2$, $R_3$, $R_4$, $R_5$, $R_6$ and m are as defined above, and $R_8$ is an amino-protecting group such as a chloroacetyl group, a formyl group, a triphenylmethyl group, a t-butoxycarbonyl group, a p-methoxybenzyloxycarbonyl group or a trimethylsilyl group.

The first step is a step of condensing a carboxylic acid of the formula II or a salt or reactive derivative thereof with an amino compound of the formula III or a salt thereof. In the case where the carboxylic acid of the formula II is used in the form of the carboxylic acid or its salt, a suitable condensation agent is employed. As such a condensation agent, there may be mentioned an N,N'-di-substituted carbodiimide such as N,N'-dicyclohexyl carbodiimide, N-ethoxycarbonyl-2-ethoxy-1,2- dihydroquinoline, phosphorus oxychloride, thionyl chloride, or oxal chloride. As the reactive derivative of the carboxylic acid of the formula II, there may be mentioned an acid halide, an acid anhydride, a mixed acid anhydride or an active ester.

As the salt of the amino compound of the formula III, there may be mentioned an inorganic salt such as a sodium salt, a potassium salt, a calcium salt or a magnesium salt, or a salt with an organic base such as triethylamine or triethanolamine.

The above condensation reaction is conducted usually in the presence or absence of a base in a suitable solvent at a temperature of from $-50°$ to $50°$ C. As the base, there may be mentioned an inorganic base such as sodium hydroxide, potassium hydroxide, sodium hydrogencarbonate, potassium hydrogencarbonate, sodium carbonate or potassium carbonate, or an organic base such as trimethylamine, triethylamine, pyridine, N-methyl morpholine, dimethylamine, dicyclohexylamine or diethylamine. As the solvent, there may be mentioned tetrahydrofuran, dioxane, chloroform, dimethylformamide, dimethylacetamide, ethyl acetate, acetone, water, or a mixture thereof.

The compound of the formula II or the salt or reactive derivative thereof is used usually in an amount of from 1 to a few mols relative to 1 mol of the compound of the formula III. The reaction time is usually from 10 minutes to 48 hours.

The step of removing the protective groups may be conducted by a common method based on the properties of the protective groups for the amino or carboxy group to remove the amino-protecting group as $R_8$ and optionally the carboxy-protecting group as $R_4$ in the compound of the formula IV.

PROCESS B

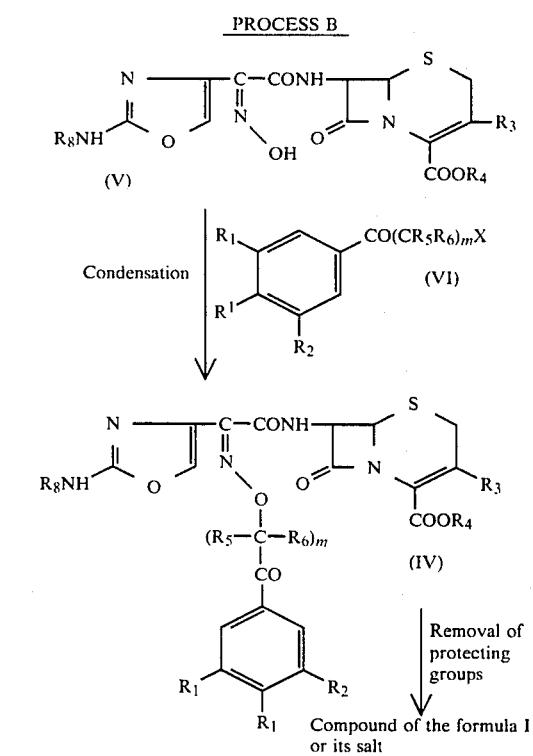

In the above formulas, $R_1$, $R_2$, $R_3$, $R_4$, $R_5$, $R_6$, $R_8$ and m are as defined above, and X is a halogen atom.

The step of the condensation can be carried out by reacting the hydroxyimino compound of the formula V with the compound of the formula VI in the presence or absence of a base in a suitable solvent at a temperature of from $-50°$ to $50°$ C. In the case where the reaction is conducted in the presence of a base, there may be employed a base similar to the one used in the step of the condensation in process A as such a base. The compound of the formula VI is used usually in an amount of from 1 to a few mols relative to 1 mol of the compound of the formula V. The reaction time is usually from 10 minutes to 48 hours. The step for the removal of protecting groups may be conducted in the same manner as in process A.

As shown in Table 1, compounds of the formula I obtained by the present invention, exhibit excellent antibiotic activities, and they are extremely effective for curing infectious diseases caused by gram-positive bacteria such as Staphylococcus aureus, and gram-negative bacteria such as Escherichia coli, Proteus vulgaris or Pseudomonas aeruginosa.

As a comparative substance, Cefotaxime having the following structure was employed.

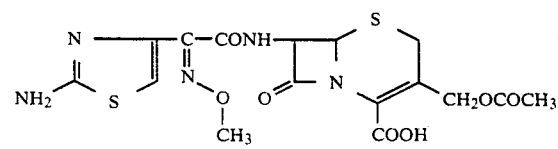

TABLE 1

| Bacteria | Minimum inhibitory concentration (μg/ml) | | | | | | | | | | |
|---|---|---|---|---|---|---|---|---|---|---|---|
| | Test Compounds | | | | | | | | | | |
| | Example 1 | Example 2 | Example 3 | Example 4 | Example 5 | Example 6 | Example 7 | Example 8 | Example 9 | Example 10 | Cefotaxime |
| *Staphylococcus aureus* JC-1 | 3.12 | 3.12 | 12.5 | 1.56 | 1.56 | 3.12 | 12.5 | 1.56 | 3.12 | 6.25 | 6.25 |
| *Escherichia coli* JC-2 | 0.78 | 0.2 | 0.2 | 0.2 | 0.39 | 0.2 | 0.05 | 0.1 | 0.2 | 0.05 | 0.1 |
| *Klebsiella pneumoniae* KC-1 | 0.2 | 0.05 | 0.05 | 0.2 | 0.2 | 0.05 | <0.05 | 0.1 | 0.05 | 0.2 | 0 |
| *Proteus vulgaris* GN-76 | 1.56 | 1.56 | 1.56 | 0.39 | 0.39 | 0.2 | 0.1 | 0.39 | 0.2 | 0.05 | 0.05 |
| *Pseudomonus aeruginosa* GN1036 | 0.78 | 0.2 | 0.2 | 0.78 | 0.39 | 0.39 | 0.05 | 0.39 | 0.2 | 0.39 | 12.5 |
| *Pseudomonus aeruginsoa* Y-1 | 0.1 | 0.05 | <0.05 | 0.1 | 0.1 | 0.1 | <0.05 | 0.1 | 0.05 | 0.1 | 12.5 |

Now, the present invention will be described in further detail with reference to Reference Examples and Working Examples. However, it should be understood that the present invention is by no means restricted by these specific Examples.

REFERENCE EXAMPLE 1

Synthesis of 2-(2-chloroacetamidooxazol-4-yl)-2-Z-hydroxyimino-acetic acid benzhydryl ester

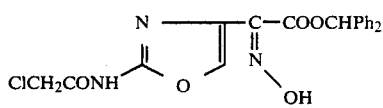

(1) In 20 ml of dimethylacetamide, 3.66 g of 2-(2-aminooxazol-4-yl)-2-Z-(2-tetrahydropyranyloxyimino)acetic acid methyl ester was suspended and cooled with ice. After the dropwise addition of 1.23 ml of chloroacetyl chloride, the mixture was stirred for 30 minutes under cooling with ice and 30 minutes at room temperature. After the reaction, ethyl acetate was added, and the mixture was washed with water and then with a saturated sodium chloride aqueous solution, dried over anhydrous magnesium sulfate and then concentrated under reduced pressure, whereby crystals of 2-(2-chloroacetamidooxazol-4-yl)-2-Z-(2-tetrahydropyranyloxyimino)acetic acid methyl ester precipitated. Ethyl ether was added, and the crystals were collected by filtration.

Yield: 4.26 g
IR(KBr)$\nu$(cm$^{-1}$): 1750, 1625, 1560, 1260
NMR(CDCl$_3$)$\delta$(ppm): 3.96 (3H, s, COOCH$_3$) 4.31 (2H, s, ClCH$_2$CO) 5.37 (1H, br, —O—CH—O—) 7.72 (1H, s, Oxazole 5-CH)

(2) In 200 ml of ethanol, 9.41 g of the compound obtained in Reference Example 1-(1) was suspended, and after the addition of 10.8 ml of a 10N sodium hydroxide aqueous solution, the mixture was stirred at room temperature for 20 minutes. Then, 400 ml of ethyl acetate was added to the reaction solution, and the reaction mixture was washed with a cool aqueous sodium chloride solution containing 200 ml of 1N hydrochloric acid and then with a saturated sodium chloride aqueous solution. The washing solution was extracted with 200 ml of ethyl acetate, and the ethyl acetate extract was joined to the organic layer. The organic layer was dried over anhydrous magnesium sulfate, and then concentrated under reduced pressure. Then, 150 ml of ethyl ether was added, and the mixture was cooled with ice, whereby crystals of 2-(2-chloroacetamidooxazol-4-yl)-2-Z-(2-tetrahydropyranyloxyimino)acetic acid precipitated. The crystals were collected by filtration.

Yield: 7.50 g
IR(KBr)$\nu$(cm$^{-1}$): 1745, 1625, 1540
NMR(CDCl$_3$)$\delta$(ppm): 4.27 (2H, s, ClCH$_2$CO) 5.39 (1H, br, —O—CH—O—) 7.82 (1H, s, Oxazole 5-CH)

(3) To 8.29 g of the compound obtained in Reference Example 1-(2), 20 ml of anisole and 50 ml of trifluoroacetic acid were added, and the mixture was stirred at room temperature for 30 minutes. After the reaction, the mixture was concentrated under reduced pressure, and 150 ml of ethyl ether and 150 ml of n-hexane were sequentially added, whereby 2-(2-chloroacetamidooxazol-4-yl)-2-Z-hydroxyiminoacetic acid precipitated. The precipitates were collected by filtration.

Yield: 5.78 g
IR(KBr)$\nu$(cm$^{-1}$): 1745, 1620, 1560, 1420, 1200
NMR(DMSO-d$_6$)$\delta$(ppm): 4.33 (2H, s, ClCH$_2$CO) 8.17 (1H, s, Oxazole 5-CH)

(4). In 100 ml of tetrahydrofuran, 5.70 g of the compound obtained in Reference Example 1-(3) was dissolved, and while stirring the solution at room temperature, diphenyldiazomethane was slowly added until the red color did not disappear. After the reaction, the reaction mixture was concentrated under reduced pressure and subjected to silica gel column chromatography. The eluate with chloroform:acetone=2:1 containing the desired product was collected and concentrated under reduced pressure, whereby crystals of 2-(2-chloroacetamidooxazol-4-yl)-2-Z-hydroxyiminoacetic acid benzhydryl ester precipitated. After the addition of ethyl ether and n-hexane, the crystals were collected by filtration.

Yield: 4.60 g
IR(KBr)$\nu$(cm$^{-1}$): 1735, 1620, 1585, 1205
NMR(CDCl$_3$): DMSO - d$_6$=4 : 1)$\delta$(ppm): 4.27 (2H, s, ClCH$_2$CO) 7.07 (1H, s, Ph$_2$C$\underline{H}$) 7.38 (10H, s, $\underline{Ph_2}$CH) 7.56 (1H, s, Oxazole 5-CH)

REFERENCE EXAMPLE 2

Synthesis of 2-(2-chloroacetamidooxazol-4-yl)-2-Z-(3,4-diacetoxybenzoylmethoxyimino)acetic acid

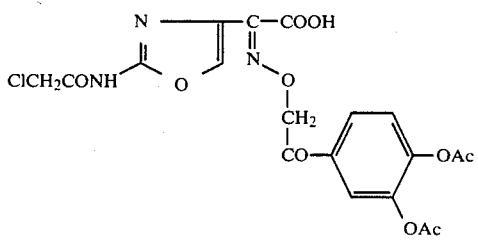

(1) In 90 ml of water, 2.61 g of 4-chloroacetylcatechol was suspended, and after the addition of 2.67 g of borax, the mixture was stirred at room temperature for 1 hour. The clear solution thereby obtained was evaporated to dryness under reduced pressure, and the residue was dissolved in 35 ml of dimethyl sulfoxide. After the addition of 50 ml of benzene thereto, the mixture was concentrated under reduced pressure, and remaining water was azeotropically removed. To the dimethyl sulfoxide solution of 4-chloroacetylcatechol borate thereby obtained, 2.90 g of 2-(2-chloroacetamidooxazol-4-yl)-2-Z-hydroxyiminoacetic acid benzhydryl ester obtained in Reference Example 1 and 3.87 g of anhydrous potassium carbonate were added, and the mixture was stirred at room temperature for 17 hours. Then, the mixture was diluted with ethyl acetate, washed with 1N hydrochloric acid and then with a saturated sodium chloride aqueous solution, dried over anhydrous magnesium sulfate and evaporated to dryness under reduced pressure. The residue was dissolved in 30 ml of tetrahydrofuran, and after the addition of 3.5 ml of pyridine and 3.5 ml of acetic anhydride, the mixture was stirred at room temperature for 1.5 hours. After the addition of ice water and ethyl acetate, the organic layer was washed sequentially with 1N hydrochloric acid, a 0.5N sodium hydrogencarbonate aqueous solution and a saturated sodium chloride aqueous solution, dried over anhydrous magnesium sulfate, and then concentrated under reduced pressure. The residue was subjected to silica gel column chromatography. The fraction containing the desired product eluted with chloroform:acetone=15:1–10:1, was evaporated to dryness under reduced pressure, and the residue was dissolved in 20 ml of ethyl acetate, and dropwise added to 100 ml of n-hexane, whereby 2-(2-chloroacetamidooxazol-4-yl)-2-Z-(3,4-diacetoxybenzoylmethoxyimino)acetic acid benzhydryl ester precipitated. The precipitates were collected by filtration.

Yield: 2.30 g

IR(KBr)$\nu$(cm$^{-1}$): 1780, 1775, 1630, 1375, 1260, 1200

NMR(CDCl$_3$)$\delta$(ppm): 2.28 (6H, s, 2xOAc) 4.18 (2H, s, ClCH$_2$CO) 5.32 (2H, s, OCH$_2$CO) 7.38 (10H, s, Ph$_2$CH)

(2) In 1 ml of anisole and 5 ml of trifluoroacetic acid, 625 mg of the compound obtained in Reference Example 2-(1) was dissolved, and stirred at room temperature for 30 minutes. After the reaction, the reaction mixture was concentrated under reduced pressure, and 30 ml of ethyl ether and 10 ml of n-hexane were added, whereby 2-(2-chloroacetamidooxazol-4-yl)-2-Z-(3,4-diacetoxybenzoylmethoxyimino)acetic acid precipitated. The precipitates were collected by filtration.

Yield 471 mg

IR(KBr)$\nu$(cm$^{-1}$): 1775, 1615, 1375, 1260, 1200

NMR(CDCl$_3$)$\delta$(ppm): 2.30 (6H, s, 2xOAc) 4.22 (2H, s, ClCH$_2$CO) 5.52 (2H, s, OCH$_2$CO)

REFERENCE EXAMPLE 3

Synthesis of 2-(2-chloroacetamidooxazol-4-yl)-2-(3,4-diacetoxybenzoyloxyimino)acetic acid

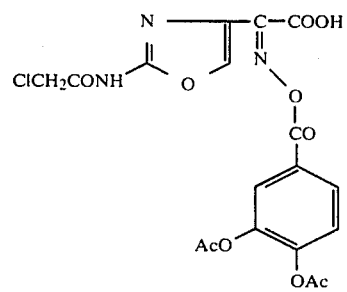

(1) In 25 ml of benzene, 1.79 g of 3,4-diacetoxybenzoic acid was suspended, and after the addition of 0.05 ml of dimethylformamide and 2.72 ml of thionyl chloride, the mixture was refluxed under heating for 1 hour. After the reaction, the solvent was distilled off, and the acid chloride thereby obtained was dissolved in 5 ml of tetrahydrofuran and subjected to the following reaction.

In 25 ml of tetrahydrofuran, 2.07 g of 2-(2-chloroacetamidooxazol-4-yl)-2-hydroxyiminoacetic acid benzhydryl ester obtained in Reference Example 1 was dissolved, and after the addition of 2 ml of pyridine, the mixture was stirred under cooling with ice. To this stirred solution, the tetrahydrofuran solution of the acid chloride prepared above, was added, and the mixture was stirred under cooling with ice for 1 hour. After the addition of ice water and ethyl acetate, the mixture was acidified with 20 ml of 1N hydrochloric acid, and the organic layer was separated. The aqueous layer was extracted with 50 ml of ethyl acetate, and the ethyl acetate extract was joined to the organic layer. The organic layer was washed with a saturated sodium chloride aqueous solution, dried over anhydrous magnesium sulfate and then evaporated to dryness under reduced pressure.

The residue was subjected to silica gel column chromatography and eluted with chloroform:acetone=30:1–5:1. The fraction containing the desired product was collected and evaporated to dryness under reduced pressure. The residue was dissolved in a small amount of ethyl acetate, and dropwise added to n-hexane, whereby 2-(2-chloroacetamidooxazol-4-yl)-2-(3,4-diacetoxybenzoyloxyimino)acetic acid benzhydryl ester precipitated. The precipitates were collected by filtration.

Yield: 2.77 g

IR(KBr)$\nu$(cm$^{-1}$): 1780, 1630, 1380, 1280, 1270, 1200

NMR(CDCl$_3$)$\delta$(ppm): 2.26, 2.30 (6H, each s, 2xOAc) 4.34 (2H, s, ClCH$_2$CO) 7.31 (10H, s, Ph$_2$CH) 7.65 (1H, s, Oxazole 5-CH)

(2) To 2.68 g of the compound obtained in Reference Example 3-(1), 3 ml of anisole and 15 ml of trifluoroacetic acid were added, and the mixture was stirred at room temperature for 30 minutes. Then, the reaction solution was concentrated under reduced pressure, and after the addition of 40 ml of ethyl ether and 20 ml of n-hexane, the mixture was cooled with ice, whereby 2-(2-chloroacetamidooxazol-4-yl)-2-(3,4-diacetoxybenzoyloxyimino)acetic acid precipitated. The precipitates were collected by filtration.

Yield: 1.73 g

IR(KBr)ν(cm$^{-1}$) 1760, 1625, 1560, 1280, 1270, 1205

NMR(CDCl$_3$:DMSO - d$_6$=4:1)δ(ppm): 2.32 (6H, s, 2xOAc) 4.30 (2H, s, ClCH$_2$CO) 7.92 (1H, s, Oxazole 5-CH)

REFERENCE EXAMPLE 4

Synthesis of 2-(2-chloroacetamidooxazol-4-yl)-2-(3,4,5-triacetoxybenzoyloxyimino)acetic acid

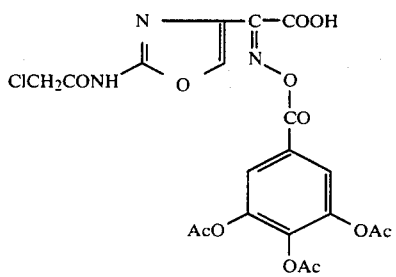

(1) In 15 ml of benzene, 1.33 g of 3,4,5-triacetoxybenzoic acid was suspended, and after the addition of 0.05 ml of dimethylformamide and 1.63 ml of thionyl chloride, the mixture was refluxed under heating for 1 hour. After the reaction, the solvent was distilled off, and the acid chloride thereby obtained was dissolved in 5 ml of tetrahydrofuran.

In 15 ml of tetrahydrofuran, 1.24 g of 2-(2-chloroacetamidooxazol-4-yl)-2-hydroxyiminoacetic acid benzhydryl ester obtained in Reference Example 1 was dissolved, and 1.5 ml of pyridine was added. While stirring the mixture under cooling with ice, the acid chloride solution prepared above was added, and the mixture was stirred under cooling with ice for 20 minutes.

After the reaction, ice water and 50 ml of ethyl acetate were added to the reaction solution, and the mixture was acidified with 15 ml of 1N hydrochloric acid. The organic layer was separated. The aqueous layer was extracted with 50 ml of ethyl acetate, and the ethyl acetate extract was joined to the organic layer. The organic layer was washed with a saturated sodium chloride aqueous solution, dried over anhydrous magnesium sulfate, and evaporated to dryness under reduced pressure. The residue was subjected to silica gel column chromatography, and the fraction containing the desired product eluted with chloroform:acetone=30:1–20:1, was collected and evaporated to dryness under reduced pressure. The residue was dissolved in a small amount of ethyl acetate and dropwise added to n-hexane, whereby 2-(2-chloroacetamidooxazol-4-yl)-2-(3,4,5-triacetoxybenzoyloxyimino)acetic acid benzhydryl ester precipitated. The precipitates were collected by filtration. The yield was 2.07 g. The precipitates contained a small amount of n-hexane.

IR(KBr)ν(cm$^{-1}$): 1790, 1630, 1440, 1375, 1330, 1190

NMR(CDCl$_3$)δ(ppm): 2.30 (9H, s, 3xOAc) 4.31 (2H, s, ClCH$_2$CO) 7.21 (1H, s, Ph$_2$C$\underline{H}$) 7.29 (10H, s, P$\underline{h_2}$CH) 7.63 (2H, s, Aromatic ring CH) 7.85 (1H, s, Oxazole 5-CH)

(2) To 2.07 g of the compound obtained in Reference Example 4-(1), 2 ml of anisole and 10 ml of trifluoroacetic acid were added, and the mixture was stirred at room temperature for 30 minutes. After the reaction, the reaction solution was concentrated under reduced pressure, and 50 ml of ethyl ether was added thereto, whereby 2-(2-chloroacetamidooxazol-4-yl)-2-(3,4,5-triacetoxybenzoyloxyimino)acetic acid precipitated. The precipitates were collected by filtration.

Yield: 1.25 g

IR(KBr)ν(cm$^{-1}$): 1790, 1620, 1560, 1500, 1440, 1380, 1330 , 1190

NMR(CDCl$_3$:DMSO - d$_6$=4:1)δ(ppm): 2.31 (9H, s, 3 xOAc) 4.28 (2H, s, ClCH$_2$CO) 7.81 (2H, s, Aromatic ring CH) 8.11 (1H, s, Oxazole 5-CH)

REFERENCE EXAMPLE 5

Synthesis of 7β-[2-(2-chloroacetamidooxazol-4-yl)-2-Z-hydroxyiminoacetamido]-3-(1-methyl-1H-tetrazol-5-yl)-thiomethyl-3-cephem-4-carboxylic acid benzhydryl ester

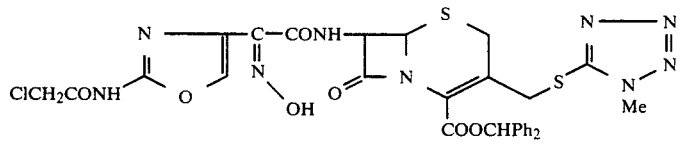

(1) Into a mixed solution comprising 10 ml of dimethylformamide and 50 ml of tetrahydrofuran, 3.32 g of 2-(2-chloroacetamidooxazol-4-yl)-2-Z-(2-tetrahydropyranyloxyimino)acetic acid obtained in Reference Example 1-(2) and 4.95 g of 7β-amino-3-(1-methyl-1H-tetrazol-5-yl) thiomethyl-3-cephem-4-carboxylic acid benzhydryl ester were dissolved. While stirring the solution under cooling with ice, 2.06 g of dicyclohexylcarbodiimide dissolved in 20 ml of tetrahydrofuran was added over a period of 1 hour. After the addition, the mixture was stirred under cooling with ice for 1 hour. After the reaction, the precipitated crystals of urea were removed by filtration, and the filtrate was concentrated under reduced pressure. Then, after the addition of water, the mixture was extracted twice with 100 ml of ethyl acetate. The organic layer was washed sequentially with water and a saturated sodium chloride aqueous solution, dried over anhydrous magnesium sulfate and evaporated to dryness under reduced pressure. The residue was subjected to silica gel column chromatography, and the fraction containing the desired product eluted with chloroform:acetone=5:1–3:1, was evaporated to dryness under reduced pressure. The residue was dissolved in 20 ml of ethyl acetate and then dropwise added to n-hexane, whereby 7β-[2-(2-chloroacetamidooxazol-4-yl)-2-Z-(2tetrahydropyranyloxyimono)acetamido]-3-(1-methyl-1H-tetrazol-5-yl)thiomethyl-3-cephem-4-carboxylic acid benzhydryl ester precipitated. The precipitates were collected by filtration.

Yield: 4.21 g

IR(KBr)ν(cm$^{-1}$): 1790, 1740, 1700, 1625

NMR(CDCl$_3$)δ(ppm): 3.80 (3H, s, Tetrazole 1-CH$_3$) 5.33 (1H, br s, OCHO) 6.95 (1H, s, Ph$_2$C$\underline{H}$) 7.33 (10H, s, P$\underline{h_2}$CH) 7.90, 7.93 (1H, s, Oxazole 5-C$\overline{H}$)

(2) Into a mixed solution of 4 ml of anisole and 20 ml of trifluoroacetic acid, 4.04 g of the compound obtained in Reference Example 5-(1) was dissolved, and the solution was stirred at room temperature for 30 minutes. Then, 100 ml of ethyl ether and 50 ml of n-hexane were added thereto, whereby 7β-[2-(2-chloroacetamidooxazol-4-yl)-2-Z-hydroxyiminoacetamido]-3-(1-methyl-1H-tetrazol-5-yl)-thiomethyl-3-cephem-4-carboxylic acid precipitated. The precipitates were collected by filtration.

Yield: 3.01 g

IR(KBr)ν(cm$^{-1}$): 1790, 1740, 1690, 1630, 1560, 1400

NMR(DMSO - d$_6$)δ(ppm): 3.96 (3H, s, Tetrazole 1-CH$_3$) 4.39 (2H, s, ClCH$_2$CO) 8.00 (1H, s, Oxazole 5-CH)

(3) In 30 ml of acetone, 2.91 g of 7β-[2-(2-chloroacetamidooxazol-4-yl)-2-Z-hydroxyiminoacetamido]-3-(1-methyl-1H-tetrazol-5-yl)thiomethyl-3-cephem-4-carboxylic acid was dissolved, and diphenyldiazomethane was slowly added until the red color did not disappear.

After the reaction, the solvent was distilled off under reduced pressure. The residue was dissolved in 20 ml of ethyl acetate, and the solution was dropwise added to 100 ml of ethyl ether. Then, 50 ml of n-hexane was added, whereby 7β-[2-(2-chloroacetamidooxazol-4-yl)-2-Z-hydroxyiminoacetamido]-3-(1-methyl-1H-tetrazol-5-yl)-thiomethyl-3-cephem-4-carboxylic acid benzhydryl ester precipitated. The precipitates were collected by filtration.

Yield: 3.29 g

IR(KBr)ν(cm$^{-1}$): 1790, 1740, 1625, 1390, 1240

NMR(DMSO - d$_6$)δ(ppm): 3.88 (3H, s, Tetrazole 1-CH$_3$) 4.41 (2H, s, ClCH$_2$CO) 6.92 (1H, s, Ph$_2$CH) 7.39 (10H, s, Ph$_2$CH) 8.03 (1H, s, Oxazole 5-CH)

EXAMPLE 1

Synthesis of 7β-[2-(2-aminooxazol-4-yl)-2-Z-(3,4-diacetoxybenzoylmethoxyimino)acetamido]cephalosporanic acid

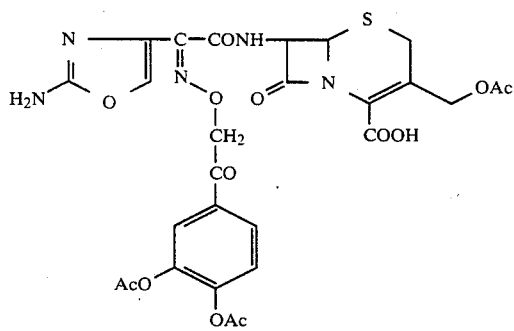

(1) In 10 ml of ethyl acetate, 471 mg of 2-(2-chloroacetamidooxazol-4-yl)-2-Z-(3,4-diacetoxybenzoylmethoxyimino)acetic acid obtained in Reference Example 2 was dissolved. While stirring the mixture under cooling with ice, 322 mg of 7-aminocephalosporanic acid t-butyl ester and 202 mg of dicyclohexylcarbodiimide were added, and the mixture was stirred under cooling with ice for 1 hour. The precipitated crystals were removed by filtration, and the filtrate was concentrated under reduced pressure and subjected to silica gel column chromatography. The fraction containing the desired product eluted with chloroform:acetone=3:1, was evaporated to dryness under reduced pressure. The residue was dissolved in 5 ml of ethyl acetate and dropwise added to n-hexane, whereby 7β-[2-(2-chloroacetamidooxazol-4-yl)-2-Z-(3,4-diacetoxybenzoylmethoxyimino)acetamido]cephalosporanic acid t-butyl ester precipitated. The precipitates were collected by filtration.

Yield: 510 mg

IR(KBr)ν(cm$^{-1}$): 1785, 1740, 1625, 1375, 1200

NMR(CDCl$_3$)δ(ppm): 1.55 (9H, s, t-Bu) 2.06 (3H, s, OAc) 2.30 (6H, s, 2xOAc) 4.21 (2H, s, ClCH$_2$CO) 5.51 (2H, s, OCH$_2$CO) 7.84 (1H, s, Oxazole 5-CH)

(2) In 15 ml of dimethylformamide, 1.82 g of the compound obtained in Example 1-(1) was dissolved, and after the addition of 343 mg of thiourea, the mixture was stirred at room temperature for 2 hours. To the reaction solution, 50 ml of acetone and 100 ml of ethyl acetate were added, and the mixture was washed sequentially with water and a saturated sodium chloride aqueous solution. The aqueous layer was extracted with 100 ml of ethyl acetate, and the ethyl acetate extract was joined to the organic layer. The organic layer was dried over anhydrous magnesium sulfate, and then the solvent was distilled off. The residue was subjected to Sephadex LH-20 column chromatography, and the fraction containing the desired product eluted with acetone was evaporated to dryness under reduced pressure. The residue was dissolved in 10 ml of ethyl acetate, and the solution was dropwise added to a solvent mixture of 100 ml of n-hexane and 50 ml of ethyl ether, whereby 7β-[2-(2-aminooxazol-4-yl)-2-Z-(3,4-diacetoxybenzoylmethoxyimino)acetamido]cephalosporanic acid t-butyl ester precipitated. The precipitates were collected by filtration.

Yield: 1.12 g

IR(KBr)ν(cm$^{-1}$): 1790, 1740, 1670, 1375, 1260, 1200

NMR(CDCl$_3$)δ(ppm): 1.55 (9H, s, t-Bu) 2.07 (3H, s, OAc) 2.30 (6H, s, 2xOAc) 5.48 (2H, br s, OCH$_2$CO) 7.47 (1H, s, Oxazole 5-CH)

(3) In 5 ml of trifluoroacetic acid, 728 mg of the compound obtained in Example 1-(2) was dissolved, and the solution was stirred at room temperature for 0.5 hour. After the reaction, 50 ml of ethyl ether and 50 ml of n-hexane were added thereto, whereby a trifluoroacetate of 7β[2-(2-aminooxazol-4-yl)-2-Z-(3,4-diacetoxybenzoylmethoxyimino)acetamido]cephalosporanic acid precipitated. The precipitates were collected by filtration.

Yield: 721 mg

IR(KBr)ν(cm$^{-1}$): 1790, 1735, 1430, 1380, 1265, 1200

NMR(CDCl$_3$:DMSO - d$_6$=4:1)δ(ppm): 2.06 (3H, s, OAc) 2.31 (6H, s, 2xOAc) 3.49 (2H, br, 2-CH$_2$) 5.57 (2H, br s, OCH$_2$CO)

In 5 ml of water, 720 mg of the above-mentioned trifluoroacetate was suspended, and 2.7 ml of 0.5N sodium hydrogencarbonate was slowly added to dissolve the precipitates. A small amount of insoluble matter was removed by filtration, and the filtrate was concentrated under reduced pressure. A mixture of ethyl alcohol and ethyl ether was added thereto, whereby a sodium salt of 7β-[2-(2-aminooxazol-4-yl)-2-Z-(3,4-diacetoxybenzoylmethoxyimino)acetamido]cephalosporic acid precipitated. The precipitates were collected by filtration.

Yield: 515 mg

EXAMPLE 2

Synthesis of 7β-[2-(2-aminooxazol-4-yl)-2-Z-(3,4-diacetoxybenzoylmethoxyimino)acetamido]-3-(1-methyl-1H-tetrazol-5-yl)thiomethyl-3-cephem-4-carboxylic acid

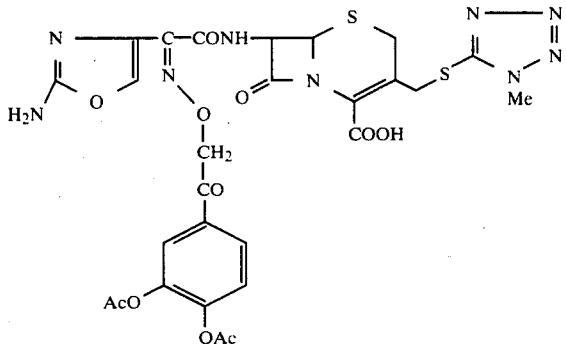

(1) In 15 ml of tetrahydrofuran, 686 mg of (2-(2-chloroacetamidooxazol-4-yl)-2-Z-(3,4-diacetoxybenzoylmethoxyimino)acetic acid obtained in Reference Example 2 and 702 mg of 7-amino-3-(1-methyl-1H-tetrazol-5-yl)thiomethyl-3-cephem-4-carboxylic acid benzhydryl ester were dissolved, and after the addition of 293 mg of dicyclohexylcarbodiimide, the mixture was stirred at room temperature for 2 hours. After the reaction, the formed crystals of urea were removed by filtration, and the filtrate was evaporated to dryness under reduced pressure. The residue was subjected to silica gel column chromatography, and the fraction containing the desired product eluted with chloroform:acetone=5:1, was collected, and the solvent was distilled off. The residue was dissolved in a small amount of ethyl acetate, and dropwise added to n-hexane, whereby 7β-[2-(2-chloroacetamidooxazol-4-yl)-2-Z-(3,4-diacetoxybenzoylmethoxyimino)acetamido]-3-(1-methyl-1H-tetrazol-5-yl)thiomethyl-3-cephem-4-carboxylic acid benzhydryl ester precipitated. The precipitates were collected by filtration.

Yield: 620 mg

IR(KBr)ν(cm$^{-1}$): 1790, 1780, 1740, 1700, 1620, 1375, 1260, 1200

NMR(CDCl$_3$)δ(ppm): 2.26 (6H, s, 2xOAc) 3.74 (3H, s, Tetrazole 1-CH$_3$) 4.18 (2H, s, ClCH$_2$CO) 3.85 (2H, br s, OCH$_2$CO) 6.94 (1H, s, Ph$_2$CH) 7.34 (10H, s, PH$_2$CH) 7.84 (1H, s, Oxazole 5-CH)

(2) In 10 ml of dimethylformamide, 620 mg of the compound obtained in Example 2-(1) was dissolved, and after the addition of 98 mg of thiourea, the mixture was stirred at room temperature for 3 hours. After the reaction, acetone, ethyl acetate and water were added, and the organic layer was separated, washed with a saturated sodium chloride aqueous solution and dried over anhydrous magnesium sulfate, and then the solvent was distilled off under reduced pressure. The residue was subjected to silica gel column chromatography, and the fraction containing the desired product eluted with chloroform:acetone=3:1–2:1 was collected and evaporated to dryness under reduced pressure. The residue was dissolved in 5 ml of ethyl acetate and dropwise added to n-hexane, whereby 7β-[2-(2-aminooxazol-4-yl)-2-Z-(3,4-diacetoxybenzoylmethoxyimino)acetamido]-3-(1-methyl-1H-tetrazol-5-yl)thiomethyl-3-cephem-4-carboxylic acid benzhydryl ester precipitated. The precipitates were collected by filtration.

Yield: 275 mg

IR(KBr)ν(cm$^{-1}$): 1785, 1670, 1375, 1260, 1200

NMR(CDCl$_3$)δ(ppm): 2.27 (6H, s, 2xOAc) 3.75 (3H, s, Tetrazole 1-CH$_3$) 5.48 (2H, br s, OCH$_2$CO) 6.93 (1H, s, Ph$_2$CH) 7.32 (10H, s, Ph$_2$CH) 7.47 (1H, s, Oxazole 5-CH)

(3) To 247 mg of the compound obtained in Example 2-(2), 0.5 ml of anisole and 2.5 ml of trifluoroacetic acid were added, and the mixture was stirred under cooling with ice for 0.5 hour. The reaction mixture was dropwise added to a mixed solution comprising 40 ml of diisopropyl ether and 20 ml of n-hexane, whereby a trifluoroacetate of 7β-[2-(2-aminooxazol-4-yl)-2-Z-(3,4-diacetoxybenzoylmethoxyimino)acetamido]-3-(1-methyl-1H-tetrazol-5-yl)thiomethyl-3-cephem-4-carboxylic acid precipitated. The precipitates were collected by filtration.

Yield: 238 mg

IR(KBr)ν(cm$^{-1}$): 1780, 1730, 1375, 1265, 1200

NMR[(CD$_3$)$_2$CO]δ(ppm): 2.31 (6H, s, 2xOAc) 3.79 (2H, br s, 2-CH$_2$) 3.96 (3H, s, Tetrazole 1-CH$_3$) 5.72 (2H, br s, OCH$_2$CO) 7.79 (1H, s, Oxazole 5-CH)

In water, 237 mg of the above trifluoroacetate was suspended, and dissolved by slowly adding an aqueous sodium hydrogencarbonate solution. The solution was subjected to Amberlite XAD-2 column chromatography, whereby 170 mg of a sodium salt of 7β-[2-(2-aminooxazol-4-yl)-2-Z-(3,4-diacetoxybenzoylmethoxyimino)acetamido]-3-(1-methyl-1H-tetrazol-5-yl)thiomethyl-3-cephem-4-carboxylic acid was obtained from the eluate with ethanol:water=4:1.

EXAMPLE 3

Synthesis of 7β-[2-(2-aminooxazol-4-yl)-2-Z-(3,4-diacetoxybenzoylmethoxyimino)]acetamido-3-(1-carboxymethyl-1H-tetrazol-5-yl)thiomethyl-3-cephem-4-carboxylic acid

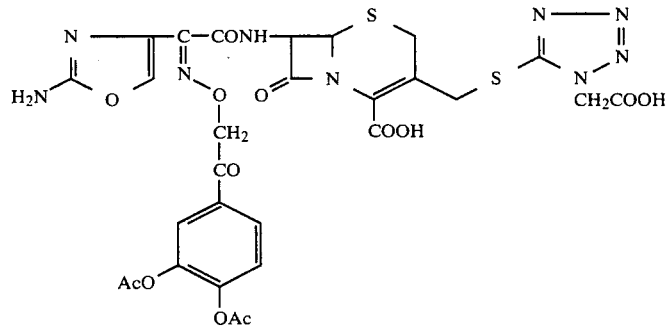

(1) In 15 ml of tetrahydrofuran, 0.723 g of 2-(2-chloroacetamidooxazol-4-yl)-2-Z-(3,4-diacetoxybenzoylmethoxyimino)acetic acid obtained in Reference Example 2 and 1.057 g of 7-amino-3-(1-benzhydryloxycarbonylmethyl-1H-tetrazol-5-yl)thiomethyl-3-cephem-4-carboxylic acid benzhydryl ester were dissolved. After the addition of 0.309 g of dicyclohexylcarbodiimide, the mixture was stirred at room temperature for 1 hour. The crystals of urea thereby formed were removed by filtration, and the filtrate was concentrated under reduced pressure and subjected to silica gel column chromatography. The fraction containing the desired product eluted with chloroform:acetone=10:1-5:1, was evaporated to dryness under reduced pressure. The residue was dissolved in a small amount of ethyl acetate and dropwise added to n-hexane, whereby 7β-[2-(2-chloroacetamidooxazol-4-yl)-2-Z-(3,4-diacetoxybenzoylmethoxyimino)acetamido]-3-(1-benzhydryloxycarbonylmethyl-1H-tetrazol5-yl)thiomethyl-3-cephem-4-carboxylic acid benzhydryl ester precipitated. The precipitates were collected by filtration.

Yield: 1.019 g

IR(KBr)ν(cm⁻¹): 1785, 1730, 1625, 1375, 1260, 1205

NMR(CDCl₃)δ(ppm): 2.25, 2.29 (6H, each s, 2xOAc) 5.04 (2H, s, NCH₂CO) 5.49 (2H, br s, OCH₂CO) 6.88, 6.93 (2H, each s, 2xPh₂CH) 7.26, 7.33 (20H, each s, 2xPH₂CH) 7.85 (1H, s, Oxazole 5-CH)

(2) In 15 ml of dimethylformamide, 1.018 g of the compound obtained in Example 3-(1) was dissolved, and after the addition of 0.133 g of thiourea, the mixture was stirred at room temperature for 3 hours. After the reaction, acetone, ethyl acetate and water were added. The organic layer was separated, washed with a saturated sodium chloride aqueous solution and dried over anhydrous magnesium sulfate, and then the solvent was distilled off under reduced pressure. The residue was subjected to silica gel column chromatography. The fraction containing the desired product eluted with chloroform : acetone=5:1-3:1, was collected and evaporated to dryness under reduced pressure. The residue was dissolved in 5 ml of ethyl acetate and dropwise added to n-hexane, whereby 7β-[2-(2-aminooxazol-4-yl)-2-Z(3,4-diacetoxybenzoylmethoxyimino)acetamido]-3-(1-benzhydryloxycarbonylmethyl-1H-tetrazol-5-yl)thiomethyl-3-cephem-4-carboxylic acid benzhydryl ester precipitated. The precipitates were collected by filtration. Yield: 0.431 g
IR(KBr)ν(cm⁻¹): 1780, 1670, 1375, 1260, 1200

NMR(CDCl₃)δ(ppm): 2.24 (6H, s, 2xOAc) 5.00 (2H, s, NCH₂CO) 6.87, 6.90 (2H, each s, 2xPh₂CH) 7.24, 7.31 (20H, each s, 2xPh₂CH) 7.49 (1H, s, Oxazole 5-CH)

(3) To 430 mg of the compound obtained in Example 3-(2), 0.5 ml of anisole and 3 ml of trifluoroacetic acid were added, and the mixture was stirred under cooling with ice for 30 minutes. The reaction solution was dropwise added to a mixture of 40 ml of diisopropyl ether and 20 ml of n-hexane, whereby a trifluoroacetate of 7β-[2(2-aminooxazol-4-yl)-2-Z-(3,4-diacetoxybenzoylmethoxyimino)acetamido]-3-(1-carboxymethyl-1H-tetrazol-5-yl)thiomethyl-3-cephem-4-carboxylic acid precipitated. The precipitates were collected by filtration.

Yield: 315 mg

IR(KBr)ν(cm⁻¹) 1780, 1735, 1375, 1265, 1200

NMR[(CD₃)₂CO]δ(ppm): 2.30 (6H, s, 2xOAc) 3.76 (2H, s, 2-CH₂) 5.25 (2H, s, NCH₂CO) 5.68 (2H, br s, OCH₂CO) 7.77 (1H, s, Oxazole 5-CH)

In water, 314 mg of the trifluoroacetate obtained above, was suspended, and the precipitates were dissolved by gradually adding 1.4 ml of a 0.5N sodium hydrogen-carbonate aqueous solution. A small amount of insoluble matters were separated by filtration, and the filtrate was subjected to Amberlite XAD-2 column chromatography. The eluate with ethanol:water=4:1 was collected, concentrated under reduced pressure and freeze-dried, whereby 199 mg of a sodium salt of 7β-[2-(2-aminooxazol-4-yl)-2-Z-(3,4-diacetoxybenzoylmethoxyimino)acetamido]-3-1-carboxymethyl-1H-tetrazol-5-yl)thiomethyl-3-cephem-4carboxylic acid was obtained.

EXAMPLE 4

Synthesis of 7β-[2-(2-aminooxazol-4-yl)-2-Z-(3,4-diacetoxybenzoyloxyimino)acetamido]cephalosporanic acid.

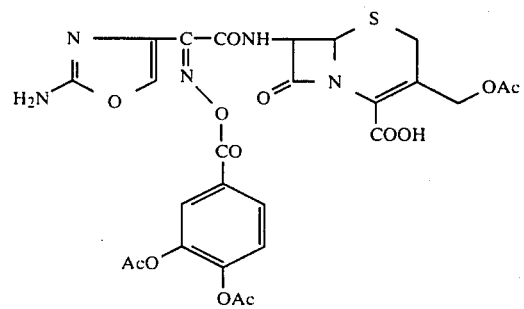

(1) In 10 ml of tetrahydrofuran, 849 mg of 2-(2-chloroacetamidooxazol-4-yl)-2-Z-(3,4-diacetoxybenzoyloxyimino)acetic acid obtained in Reference Example 3 was dissolved, and after the addition of 525 mg of 7-aminocephalosporanic acid t-butyl ester and 371 mg of dicyclohexylcarbodiimide, the mixture was stirred at room temperature for 45 minutes. The formed crystals were removed by filtration, and the filtrate was concentrated under reduced pressure and subjected to silica gel column chromatography. The fraction containing the desired product eluted with chloroform : acetone=3:1, was collected, and the solvent was distilled off under reduced pressure. The residue was dissolved in a small amount of ethyl acetate and dropwise added to n-hexane, whereby 7β-[2-(2-chloroacetamidooxazol-4-yl)-2-Z-(3,4-diacetoxybenzoyloxyimino)acetamido]cephalosporic acid t-butyl ester precipitated. The precipitates were collected by filtration.

Yield: 638 mg

IR(KBr)ν(cm⁻¹): 1780, 1625, 1550, 1370, 1200
NMR(CDCl₃)δ(ppm): 1.56 (9H, s, t-Bu) 2.08 (3H, s, OAc) 2.28 (6H, s, 2xOAc) 4.18 (2H, br s, ClCH₂CO) 7.87 (1H, s, Oxazole 5-CH)

(2) To 637 mg of the compound obtained in Example 4-(1), 20 ml of ethanol, 125 mg of thiourea and 69 mg of sodium hydrogencarbonate were added, and the mixture was stirred at 60° C. for 1 hour. After the reaction, 100 ml of ethyl acetate was added to the reaction solution. The mixture was washed with water and dried over anhydrous magnesium sulfate, and then the solvent was distilled off under reduced pressure. The residue was subjected to silica gel column chromatography. The fraction containing the desired product eluted with chloroform:acetone=2:1, was collected and evaporated to dryness under reduced pressure. The residue was dissolved in a small amount of ethyl acetate and dropwise added to n-hexane, whereby 7β-[2-(2-aminooxazol-4-yl)-2-Z-(3,4-diacetoxybenzoyloxyimino)acetamido]cephalosporanic acid t-butyl ester precipitated. The precipitates were collected by filtration.

Yield: 265 mg

IR(KBr)ν(cm⁻¹) 1785, 1680, 1375, 1225, 1180

(3) To 264 mg of the compound obtained in Example 4-(2), 3 ml of trifluoroacetic acid was added, and the mixture was stirred at room temperature for 30 minutes, and then concentrated under reduced pressure. To the residue, 2 ml of ethyl acetate and 50 ml of ethyl ether were added, whereby a trifluoroacetate of 7β-[2-(2-aminooxazol-4-yl)-2-Z-(3,4-diacetoxybenzoyloxyimino)acetamido]-cephalosporanic acid precipitated. The precipitates were collected by filtration.

Yield: 225 mg

IR(KBr)ν(cm⁻¹): 1780, 1430, 1380, 1200

NMR(DMSO-d₆)δ(ppm): 2.04 (3H, s, OAc) 2.33 (6H, s, 2xOAc) 3.57 (2H, br, 2-CH₂) 7.89 (1H, s, Oxazole 5-CH)

In 50 ml of water, 6.70 g of the trifluoroacetate obtained above, was suspended, and the precipitates were dissolved by gradually adding 33 ml of a 0.5N sodium hydrogencarbonate aqueous solution. A small amount of insoluble matters were removed by filtration, and the filtrate was concentrated under reduced pressure, and isopropyl alcohol was added, whereby a sodium salt of 7β-[2-(2-aminooxazol-4-yl)-2-Z-(3,4-diacetoxybenzoyloxyimino)acetamido]cephalosporic acid precipitated. The precipitates were collected by filtration.

Yield: 4.56 g

EXAMPLE 5

Synthesis of 7β-[2-(2-aminooxazol-4-yl)-2-Z-(3,4-diacetoxybenzoyloxyimino)acetamido]-3-(1-methyl-1H-tetrazol-5-yl)thiomethyl-3-cephem-4-carboxylic acid.

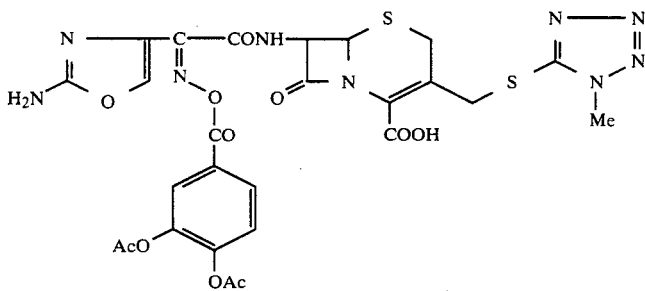

(1) In a mixed solution comprising 5 ml of dimethylformamide and 10 ml of ethyl acetate, 936 mg of 2-(2-chloroacetamidooxazol-4-yl)-2-Z-(3,4-diacetoxybenzoyloxyimino)acetic acid obtained in Reference Example 3 and 989 mg of 7-amino-3-(1-methyl-1H-tetrazol-5-yl)thiomethyl-3-cephem-4-carboxylic acid benzhydryl ester were dissolved, and 413 mg of dicyclohexylcarbodiimide was added under cooling with ice. The mixture was stirred for 1 hour under cooling with ice. After the reaction, the precipitated crystals were removed by filtration, and to the filtrate, water and ethyl acetate were added. The organic layer was separated, washed sequentially with water and a saturated sodium chloride aqueous solution, dried over anhydrous magnesium sulfate and evaporated to dryness under reduced pressure. The residue was subjected to silica gel column chromatography, and the fraction containing the desired product eluted with chloroform : acetone=4:1-3:1 was collected, and the solvent was distilled off under reduced pressure. The residue was dissolved in a small amount of ethyl acetate and then dropwise added to n-hexane, whereby 7β-[2-(2-chloroacetamidooxazol-4-yl)-2-Z-(3,4-diacetoxybenzoyloxyimino)acetamido]-3-(1-methyl-1H-tetrazol-5-yl)-thiomethyl-3-cephem-4-carboxylic acid benzhydryl ester precipitated. The precipitates were collected by filtration.

Yield: 578 mg

IR(KBr)ν(cm⁻¹) 1780, 1700, 1620, 1375, 1280, 1260, 1200

NMR(CDCl₃)δ(ppm): 2.17, 2.27 (6H, each s, 2xOAc) 3.77 (3H, s, Tetrazole 1-CH₃) 6.96 (1H, s, Ph₂CH) 7.34 (1H, s, Ph₂CH) 7.86 (1H, s, Oxazole 5-CH)

(2) In 10 ml of dimethylformamide, 2.16 g of the compound obtained in Example 5-(1) was dissolved, and after the addition of 0.347 g of thiourea, the mixture was stirred at room temperature for 2.5 hours. After the reaction, 20 ml of acetone and 50 ml of ethyl acetate were added. The mixture was washed sequentially with water and a saturated sodium chloride aqueous solution, and dried over anhydrous magnesium sulfate, and then the solvent was distilled off under reduced pressure. The residue was subjected to silica gel column chromatography, and the fraction containing the desired product eluted with chloroform:acetone=3:1-2:1, was collected and evaporated to dryness under reduced pressure. The residue was dissolved in 10 ml of ethyl acetate and dropwise added to 70 ml of n-hexane, whereby 7β-[2-(2-aminooxazol-4-yl)-2-Z-(3,4-diacetoxybenzoyloxyimino)acetamido]-3-(1-methyl-1H-tetrazol-5-yl)thiomethyl-3-cephem-4-carboxylic acid benzhydryl ester precipitated. The precipitates were collected by filtration.

Yield: 1.27 g

IR(KBr)ν(cm⁻¹) 1780, 1670, 1375, 1200

NMR(CDCl₃)δ(ppm): 2.15, 2.26 (6H, s, 2xOAc) 3.76 (3H, s, Tetrazole 1-CH₃) 6.96 (1H, s, Ph₂CH) 7.35 (10H, s, Ph₂CH) 7.48 (1H, s, Oxazole 5-CH)

(3) To 733 mg of compound obtained in Example 5-(2), 1 ml of anisole and 5 ml of trifluoroacetic acid were added, and the mixture was stirred under cooling with ice for 30 minutes. After the reaction, the reaction solution was dropwise added to a mixed solution comprising 40 ml of diisopropyl ether and 20 ml of n-hexane, whereby a trifluoroacetate of 7β-[2-(2-aminooxazol-4-yl)-2-Z-(3,4-diacetoxybenzoyloxyimino)acetamido]-3-(1-methyl-1H-tetrazol-5-yl)thiomethyl-3-cephem-4-carboxylic acid precipitated. The precipitates were collected by filtration.

Yield: 643 mg

IR(KBr)ν(cm⁻¹): 1780, 1740, 1380, 1285, 1270, 1200

NMR(CDCl₃: DMSO-d₆ =2:1)δ(ppm): 2.31 (6H, s, 2xOAc) 3.71 (2H, br s, 2-CH₂) 3.96 (3H, s, Tetrazole 1-CH₃) 7.68 (1H, s, Oxazole 5-CH)

EXAMPLE 6

Synthesis of 7β-[2-(2-aminooxazol-4-yl)-2-Z-(3,4-diacetoxybenzoyloxyimino)acetamido]-3-(2-methyl-1,3,4-thiadiazol-5-yl)thiomethyl-3-cephem-4-carboxylic acid.

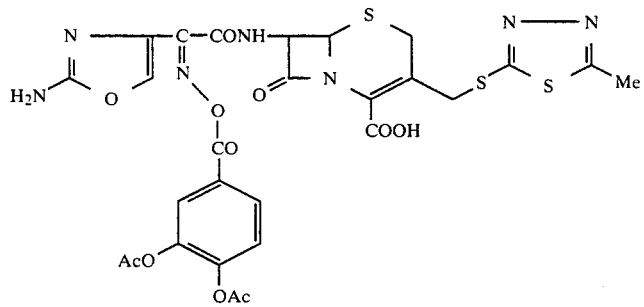

(1) Into a mixed solution comprising 5 ml of dimethylformamide and 10 ml of ethyl acetate, 0.936 g of 2-(2-chloroacetamidooxazol-4-yl)-2-Z-(3,4-diacetoxybenzoyloxyimino)acetic acid obtained in Reference Example 3 and 1.021 g of of 7-amino-3-(2-methyl-1,3,4-thiadiazol-5-yl)thiomethyl-3-cephem-4-carboxylic acid benzhydryl ester were dissolved, and 0.413 g of dicylohexylcarbodiimide was added under stirring and cooling with ice. The mixture was stirred under cooling with ice for 1 hour. After the reaction, the precipitated crystals were removed by filtration, and to the filtrate, ice water and 50 ml of ethyl acetate were added. The organic layer was washed sequentially with water and a saturated sodium chloride aqueous solution, and dried over anhydrous magnesium sulfate, and the solvent was distilled off under reduced pressure. The residue was subjected to silica gel column chromatography, and the fraction containing the desired product eluted with chloroform: acetone=3:1, was collected and evaporated to dryness under reduced pressure. The residue was dissolved in 10 ml of ethyl acetate and dropwise added to n-hexane, whereby 7β-[2-(2-chloroacetamidooxazol-4-yl)-2-Z-(3,4-diacetoxybenzoyloxyimino)acetamido]-3-(2-methyl-1,3,4-thiadiazol-5-yl)thiomethyl-3-cephem-4-carboxylic acid benzhydryl ester precipitated. The precipitates were collected by filtration.

Yield: 0.812 g

IR(KBr)ν(cm$^{-1}$): 1780, 1740, 1620, 1550, 1375, 1200
NMR(CDCl$_3$)δ(ppm): 2.18, 2.28 (6H, each s, 2xOAc) 2.61 (3H, s, Thiadiazole 2-CH$_3$) 6.98 (1H, s, Ph$_2$CH) 7.35 (10H, s, Ph$_2$CH) 7.89 (1H, s, Oxazole 5-CH)

(2) In 5 ml of dimethylformamide, 320 mg of the compound obtained in Example 6-(1) was dissolved, and after the addition of 51 mg of thiourea, the mixture was stirred at room temperature for 2 hours. After the reaction, to the reaction mixture, 50 ml of acetone and 50 ml of ethyl acetate were added. The mixture was washed sequentially with water and a saturated sodium chloride aqueous solution. The washing solution was extracted with 50 ml of ethyl acetate, and the ethyl acetate extract was joined to the organic layer. The organic layer was dried over anhydrous magnesium sulfate, and the solvent was distilled off under reduced pressure. The residue was dissolved in a small amount of ethyl acetate and dropwise added to n-hexane, whereby 7β-[2-(2-aminooxazol-4-yl)-2-Z-(3,4-diacetoxybenzoyloxyimino)acetamido]-3-(2-methyl-1,3,4-thiadiazol-5-yl)thiomethyl-3-cephem-4-carboxylic acid benzhydryl ester precipitated. The precipitates were collected by filtration.

Yield: 228 mg (3) To 228 mg of the compound obtained in Example 6-(2), 0.5 ml of anisole and 2.5 ml of trifluoroacetic acid were added, and the mixture was stirred under cooling with ice for 0.5 hour. Then, 20 ml of ethyl ether and 10 ml of n-hexane were added thereto, whereby a trifluoroacetate of 7β-[2-(2-aminooxazol-4-yl)-2-Z-(3,4-diacetoxybenzoyloxyimino)acetamido]-3-(2-methyl-1,3,4-thiadiazol5-yl)thiomethyl-3-cephem-4-carboxylic acid precipitated. The precipitates were collected by filtration.

Yield: 177 mg

IR(KBr)ν(cm$^{-1}$): 1780, 1740, 1690, 1375, 1200
NMR[(CD$_3$)$_2$CO]δ(ppm): 2.30 (6H, s, 2xOAc) 2.68 (3H, s, Thiadiazole 2-CH$_3$) 3.80 (2H, br s, 2-CH$_2$) 7.86 (1H, s, Oxazole 5-CH)

In water, 177 mg of the above trifluoroacetate was suspended, and the precipitates were dissolved by gradually adding 0.8 ml of a 0.5N sodium hydrogen-carbonate aqueous solution. A small amount of insoluble matters were removed by filtration, and the filtrate was subjected to Amberlite XAD-2 column chromatography. The eluate with ethanol : water=4:1 was collected, concentrated under reduced pressure and freeze-dried, whereby 127 mg of a sodium salt of 7β-[2-(2-aminooxazol-4-yl)-2-Z-(3,4-diacetoxybenzoyloxyimino)acetamido]-3-(2-methyl-1,3,4-thiadiazol-5-yl)thiomethyl-3-cephem-4-carboxylic acid was obtained.

EXAMPLE 7

Synthesis of 7β-[2-(2-aminooxazol-4-yl)-2-Z-(3,4-diacetoxybenzoyloxyimino)acetamido]-3-(1-carboxymethyl-1H-tetrazol-5-yl)thiomethyl-3-cephem-4-carboxylic acid

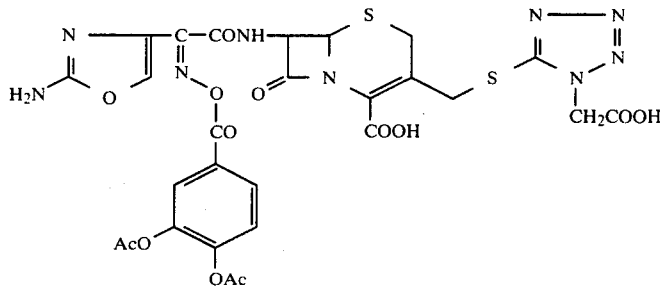

(1) In 10 ml of tetrahydrofuran, 0.936 g of 2-(2-chloroacetamidooxazol-4-yl)-2-Z-(3,4-diacetoxybenzoyloxyimino)acetic acid obtained in Reference Example 3 and 1.410 g of 7-amino-3-(1-benzhydryloxycarbonylmethyl-1H-tetrazol-5-yl)thiomethyl-3-cephem-4-carboxylic acid benzhydryl ester were dissolved, and after the addition of 0.413 g of dicyclohexylcarbodiimide, the mixture was stirred at room temperature for 30 minutes. After the reaction, the formed crystals of urea were removed by filtration, and the filtrate was concentrated under reduced pressure, and subjected to silica gel column chromatography. The fraction containing the desired product eluted with chloroform:acetone=3:1, was collected and evaporated to dryness under reduced pressure. The residue was dissolved in 10 ml of ethyl acetate and dropwise added to 100 ml of n-hexane, whereby 7β-[2-(2-chloroacetamidooxazol-4-yl)-2-Z-(3,4-diacetoxybenzoyloxyimino)acetamido]-3-(1-benzhydryloxycarbonylmethyl-1H-tetrazol-5-yl)thiomethyl-3-cephem-4-carboxylic acid benzhydryl ester precipitated. The precipitates were collected by filtration.

Yield: 1.031 g

NMR(CDCl₃)δ(ppm): 2.17, 2.32 (6H, each s, 2xOAc) 6.89, 6.97 (2H, each s, 2xPh₂CH) 7.28, 7.23 (20H, each s, 2xPh₂CH) 7.88 (1H, s, Oxazole 5-CH)

(2) In 10 ml of dimethylformamide, 1.030 g of the compound obtained in Example 7-(1) was dissolved, and 0.136 g of thiourea was added. The mixture was stirred at room temperature for 2 hours. After the reaction, to the reaction solution, 50 ml of acetone and 100 ml of ethyl acetate were added. The mixture was washed sequentially with water and a saturated sodium chloride aqueous solution and dried over anhydrous magnesium sulfate, and then the solvent was distilled off under reduced pressure. The residue was dissolved in 10 ml of ethyl acetate and then dropwise added to 80 ml of n-hexane, whereby 7β-[2-(2-aminooxazol-4-yl)-2-Z-(3,4-diacetoxybenzoyloxyimino)acetamido]-3-(1-benzhydryloxycarbonylmethyl-1H-tetrazol-5-yl)thiomethyl-3-cephem-4-carboxylic acid benzhydryl ester precipitated. The precipitates were collected by filtration.

Yield: 0.874 g

IR(KBr)ν(cm⁻¹): 1780, 1680, 1375, 1265, 1200

NMR(CDCl₃)δ(ppm): 2.13, 2.25 (6H, each s, 2xOAc) 5.04 (2H, br s, NCH₂CO) 6.86, 6.94 (2H, each s, 2xPh₂CH) 7.24, 7.31 (20H, each s, 2xPh₂CH)

(3) To 873 mg of the compound obtained in Example 7-(2), 1 ml of anisole and 5 ml of trifluoroacetic acid were added, and the mixture was stirred for 30 minutes under cooling with ice. After the reaction, 30 ml of ethyl ether and 20 ml of n-hexane were added to the reaction solution, whereby a trifluoroacetate of 7β-[2-(2-aminooxazol-4-yl)-2-Z-(3,4-diacetoxybenzoyloxyimino)-acetamido]-3-(1-carboxymethyl-1H-tetrazol-5-yl)-thiomethyl-3-cephem-4-carboxylic acid precipitated. The precipitates were collected by filtration.

Yield: 686 mg

IR(KBr)ν(cm⁻¹): 1780, 1380, 1200

NMR[(CD₃)₂CO]δ(ppm): 2.30 (6H, s, 2xOAc) 3.78 (2H, br s, 2-CH₂) 5.32 (2H, br s, NCH₂CO) 7.90 (1H, s, Oxazole 5-CH)

In water, 685 mg of the above trifluoroacetate was suspended, and the precipitates were dissolved by gradually adding 3.24 Ml of a 0.5N sodium hydrogen-carbonate aqueous solution. A small amount of insoluble matters were removed by filtration, and the filtrate was subjected to Amberlite XAD-2 column chromatography. The eluate with ethanol:water=4:1 was collected, concentrated under reduced pressure and freeze-dried, whereby 338 mg of a sodium salt of 7β-[2-(2-aminooxazol-4-yl)-2-Z-(3,4-diacetoxybenzoyloxyimino)acetamido]-3-(1-carboxymethyl-1H-tetrazol-5-yl)thiomethyl-3-cephem-4-carboxylic acid was obtained.

EXAMPLE 8

Synthesis of 7β-[2-(2-aminooxazol-4-yl)-2-Z-(3,4,5-triacetoxybenzoyloxyimino)acetamido]-3-(1-methyl-1H-tetrazol-5-yl)thiomethyl-3-cephem-4-carboxylic acid

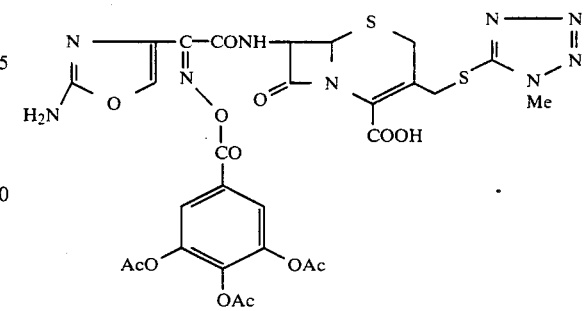

(1) In 20 ml of tetrahydrofuran, 1.196 g of 2-(2-chloroacetamidooxazol-4-yl)-2-Z-(3,4,5-triacetoxybenzoyloxyimino)acetic acid obtained in Reference Example 4 and 1.123 g of 7-amino-3-(1-methyl-1H-tetrazol-5-yl)thiomethyl-3-cephem-4-carboxylic acid benzhydryl ester were dissolved, and after the addition of 0.468 g of dicyclohexylcarbodiimide, the mixture was stirred under cooling with ice for 1 hour. After the reaction, the formed crystals of urea were removed by filtration, and the filtration was evaporated to dryness under reduced pressure and then subjected to silica gel column chromatography. The fraction containing the desired product eluted with chloroform: acetone=10:1-5:1, was collected and evaporated to dryness under reduced pressure. The residue was dissolved in a small amount of ethyl acetate and dropwise added to n-hexane, whereby 7β-[2-(2-chloroacetamidooxazol-4-yl)-2-Z-(3,4,5-triacetoxybenzoyloxyimino)acetamido]-3-(1-methyl-1H-tetrazol-5-yl)thiomethyl-3-cephem-4-carboxylic acid benzhydryl ester precipitated. The precipitates were collected by filtration.

Yield: 0.964 g

IR(KBr)ν(cm$^{-1}$): 1790, 1740, 1625, 1375, 1330, 1185

NMR(CDCl$_3$)δ(ppm): 2.16, 2.29 (9H, each s, 3xOAc)

pressure and freeze-dired, whereby 388 mg of a sodium salt of 7β-[2-(2-aminooxazol-4-yl)-2-Z-(3,4,5-triacetoxybenzoyloxyimino)acetamido]-3-(1-methyl-1H-tetrazol-5-yl)thiomethyl-3-cephem-4-carboxylic acid was obtained.

EXAMPLE 9

Synthesis of 7β-[2-(2-aminooxazol-4-yl)-2-Z-(3,4-diethoxycarbonyloxybenzoyloxyimino)acetamido]-3-(1-methyl-1H-tetrazol-5-yl)thiomethyl-3-cephem-4-carboxylic acid

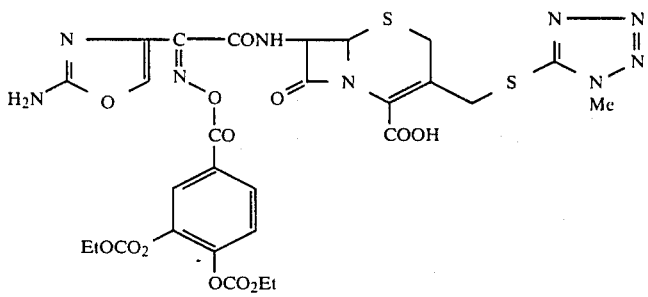

3.79 (3H, s, Tetrazole 1-CH$_3$) 6.99 (1H, s, Ph$_2$CH) 7.36 (10H, s, Ph$_2$CH) 7.79 (2H, s, Aromatic ring CH) 7.94 (1H, s, Oxazole 5-CH)

(2) In 15 ml of dimethylformamide, 963 mg of the compound obtained in Example 8-(1) was dissolved, and after the addition of 146 mg of thiourea, the mixture was stirred at room temperature for 2 hours. After the reaction, 50 ml of acetone and 100 ml of ethyl acetate were added to the reaction solution. The mixture was washed sequentially with water and a saturated sodium chloride aqueous solution. The washing solution was extracted with 100 ml of ethyl acetate, and the ethyl acetate extract was joined to the organic layer. The organic layer was dried over anhydrous magnesium sulfate, and then the solvent was distilled off under reduced pressure. The residue was dissolved in a small amount of ethyl acetate and dropwise added to n-hexane, whereby 7β-[2-(2-aminooxazol-4-yl)-2-Z-(3,4,5-triacetoxybenzoyloxyimino)acetamido]-3-(1-methyl-1H-tetrazol-5-yl)thiomethyl-3-cephem-4-carboxylic acid benzhydryl ester precipitated. The precipitates were collected by filtration. The yield was 765 mg.

(3) To 765 mg of the compound obtained in Example 8-(2), 1 ml of anisole and 5 ml of trifluoroacetic acid were added, and the mixture was stirred at room temperature for 30 minutes. To the reaction solution, 50 ml of ethyl ether and 20 ml of n-hexane were added, whereby a trifluoroacetate of 7β-[2-(2-aminooxazol-4-yl)-2-Z-(3,4,5-triacetoxybenzoyloxyimino)acetamido]-3-(1-methyl-1H-tetrazol-5-yl)thiomethyl-3-cephem-4-carboxylic acid precipitated. The precipitates were collected by filtration.

Yield: 662 mg

IR(KBr)ν(cm$^{-1}$): 1790, 1740 1435, 1375, 1330, 1180

NMR[(CD$_3$)$_2$CO]δ(ppm): 2.30 (9H, s, 3xOAc) 3.80 (2H, br s, 2-CH$_2$) 3.97 (3H, s, Tetrazole 1-CH$_3$) 7.87 (1H, s, Oxazole 5-CH) 7.90 (2H, s, Aromatic ring CH)

In water, 662 mg of the above trifluoroacetate was suspended, and 3 ml of a 0.5N sodium hydrogen carbonate aqueous solution was gradually added. A small amount of insoluble matters were removed by filtration, and the filtrate was subjected to Amberlite XAD-2 column chromatography. The eluate with ethanol: water=4:1, was collected, concentrated under reduced (1) In 20 ml of benzene, 1.342 g of 3,4-diethoxycarbonyloxybenzoic acid was suspended, and after the addition of 0.1 ml of dimethylformamide and 1.09 ml of thionyl chloride, the mixture was refluxed under heating for 1 hour. The reaction solution was evaporated to dryness under reduced pressure, and the acid chloride thereby obtained was dissolved in 5 ml of tetrahydrofuran and subjected to the following reaction.

In 15 ml of tetrahydrofuran, 1.448 g of 7β-[2-(2-chloroacetamidooxazol-4-yl)-2-Z-hydroxyiminoacetamido]-3-(1-methyl-1H-tetrazol-5-yl)thiomethyl-3-cephem-4carboxylic acid benzhydryl ester obtained in Reference Example 5 was dissolved, and 3 ml of pyridine was added thereto. While stirring the mixture under cooling with ice, the tetrahydrofuran solution of the acid chloride prepared above was added. The mixture was stirred for 1 hour under cooling with ice, and then ethyl acetate and ice water were added. The organic layer was washed sequentially with dilute hydrochloric acid, an aqueous sodium hydrogencarbonate solution and a saturated sodium chloride aqueous solution and dried over anhydrous magnesium sulfate. Then the organic layer was concentrated by removing the solvent under reduced pressure, and diisopropyl ether was added thereto, whereby 7β-[2-(2-chloroacetamidooxazol-4-yl)-2-Z-(3,4diethoxycarbonyloxybenzoyloxyiminoacetamido]-3-(1-methyl-1H-tetrazol-5-yl)thiomethyl-3-cephem-4-carboxylic acid benzhydryl ester precipitated. The precipitates were collected by filtration.

Yield: 1.936 g

IR(KBr)ν(cm$^{-1}$): 1780, 1625, 1375, 1260, 1180

NMR(CDCl$_3$: DMSO-d$_6$=4:1)δ(ppm): 1.33, 1.37 (6H, each t, J=7 Hz, 2xEtO) 3.83 (3H, s, Tetrazole 1-CH$_3$) 6.93 (1H, s, Ph$_2$CH) 7.36 (10H, s, Ph$_2$CH) 8.04 (1H, s, Oxazole 5-CH)

(2) In 30 ml of dimethylformamide, 1.935 g of the compound obtained in Example 9-(1) was dissolved, and after the addition of 0.294 g of thiourea, the mixture was stirred at room temperature for 3 hours. To the reaction solution, 60 ml of acetone and water were added. The mixture was extracted with ethyl acetate.

The organic layer was washed with a saturated sodium chloride aqueous solution and dried over anhydrous magnesium sulfate, and then the solvent was distilled off under reduced pressure. The residue was dissolved in a small amount of ethyl acetate and dropwise added to diisopropyl ether, whereby 7β-[2-(2-aminooxazol-4-yl)-2-Z-(3,4-diethoxycarbonyloxybenzoyloxyimino)acetamido]-3-(1-methyl-1H-tetrazol-5-yl)thiomethyl-3-cephem-4-carboxylic acid benzhydryl ester precipitated. The precipitates were collected by filtration.

Yield: 1.521 g

IR(KBr)ν(cm$^{-1}$) 1780, 1680, 1375, 1260, 1180

NMR(CDCl$_3$)δ(ppm): 1.31, 1.36 (6H, each t, J=7 Hz, EtO) 3.79 (3H, s, Tetrazole 1-CH$_3$) 6.98 (1H, s, Ph$_2$CH) 7.35 (10H, s, Ph$_2$CH) 7.51 (1H, s, Oxazole 5-CH)

(3) To 1.520 g of the compound obtained in Example 9-(2), 2 ml of anisole and 10 ml of trifluoroacetic acid were added, and the mixture was stirred under cooling with ice for 30 minutes. After the reaction, the reaction solution was dropwise added to a mixed solution comprising 40 ml of diisopropyl ether and 20 ml of n-hexane, whereby a trifluoroacetate of 7β-[2-(2-aminooxazol-4-yl)-2-Z-(3,4-diethoxycarbonyloxybenzoyloxyimino)acetamido]-3-(1-methyl-1H-tetrazol-5-yl)thiomethyl-3-cephem-4-carboxylic acid precipitated. The precipitates were collected by filtration.

Yield: 1.311 g

IR(KBr)ν(cm$^{-1}$) 1780, 1740, 1375, 1180

NMR[(CD$_3$)$_2$CO]δ(ppm): 1.37 (6H, each t, J=7 Hz, EtO) 3.81 (2H, br s, 2-CH$_2$) 3.98 (3H, s, Tetrazole 1-CH$_3$) 4.35 (4H, q, J=7 Hz, EtO) 7.86 (1H, s, Oxazole 5-CH)

In water, 1.310 g of the above trifluoroacetate was suspended, and the precipitates were dissolved by gradually adding 5.8 ml of a 0.5N sodium hydrogencarbonate aqueous solution. A small amount of insoluble matters were removed by filtration, and the filtrate was subjected to Amberlite XAD-2 column chromatography. The eluate with ethanol: water=4:1, was collected, concentrated under reduced pressure and freeze-dried, whereby 0.898 g of a sodium salt of 7β-[2-(2-aminooxazol-4-yl)-2-Z-(3,4-diethoxycarbonyloxybenzoyloxyimino)acetamido]-3-(1-methyl-1H-tetrazol-5-yl)thiomethyl-3-cephem-4-carboxylic acid was obtained.

EXAMPLE 10

Synthesis of 7β-[2-(2-aminooxazol-4-yl)-2-Z-(3,4,5-triacetoxybenzoyloxyimino)acetamido]-3-(1-carboxymethyl-1H-tetrazol-5-yl)thiomethyl-3-cephem-4-carboxylic acid zoyloxyimino)acetic acid obtained in Reference Example 4 and 25.67 g of 7-amino-3-(1-benzhydryloxycarbonylmethyl-1H-tetrazol-5-yl)thiomethyl-3-cephem-4-carboxylic acid benzhydryl ester were dissolved, and after the addition of 200 ml of ethyl acetate and 7.89 g of dicyclohexylcarbodiimide, the mixture was stirred at room temperature for 1 hour. After the reaction, the formed crystals of urea were removed by filtration, and the filtrate was evaporated to dryness under reduced pressure, and subjected to silica gel column chromatography. The fraction containing the desired product eluted with chloroform: acetone=10:1–5:1, was collected, and evaporated to dryness under reduced pressure. The residue was dissolved in a small amount of ethyl acetate, and dropwise added to n-hexane, whereby 7β-[2-(2-chloroacetamidooxazol-4-yl)-2-Z-(3,4,5-triacetoxybenzoyloxyimino)acetamido]-3-(1-benzhydryloxycarbonylmethyl-1H-tetrazol-5-yl)thiomethyl-3-cephem-4-carboxylic acid benzhydryl ester precipitated. The precipitates were collected by filtration.

Yield: 21.80 g

IR(KBr)ν(cm$^{-1}$): 1790, 1630, 1375, 1330, 1185

NMR(CDCl$_3$)δ(ppm): 2.14, 2.28 (9H, each s, 3xOAc) 5.07 (2H, s, CH$_2$CO$_2$) 6.90, 6.97 (2H, each s, Ph$_2$CH) 7.26, 7.34 (20H, each s, Ph$_2$CH) 7.79 (2H, s, Aromatic ring CH) 7.93 (1H, s, Oxazole 5-CH)

(2) In 50 ml of dimethylformamide, 4.85 g of the compound obtained in Example 10-(1) was dissolved, and after the addition of 1.52 g of thiourea, mixture was stirred at room temperature for 1.5 hours. After the reaction, 100 ml of acetone, 8 ml of a 0.5N sodium hydrogencarbonate aqueous solution and 100 ml of ethyl acetate were added to the reaction solution. The mixture was washed sequentially with water and a saturated sodium chloride solution. The washing solution was extracted with 100 ml of ethyl acetate, and the ethyl acetate extract was joined to the organic layer. The organic layer was dried over anhydrous magnesium sulfate, and then the solvent was distilled off under reduced pressure. The residue was subjected to Sephadex LH-20 column chromatography, and eluted with acetone. The fraction containing the desired product was collected, and the solvent was distilled off under reduced pressure. The residue was dissolved in a small amount of ethyl acetate, and dropwise added to n-hexane, whereby 7β-[2-(2-aminooxazol-4-yl)-2-Z-(3,4,5-triacetoxybenzoyloxyimino)acetamido]-3-(1-benzhydryloxycarbonylmethyl-1H-tetrazol-5-yl)thiomethyl-3-cephem-4-carboxylic acid benzhydryl ester precipitated. The precipitates were collected by filtration.

Yield: 2.48 g

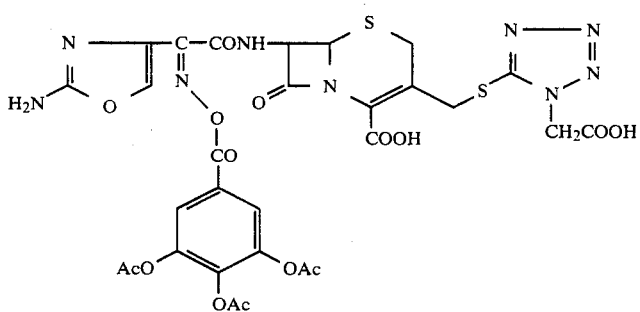

(1) In 100 ml of tetrahydrofuran, 19.15 g of 2-(2-chloroacetamidooxazol-4-yl)-2-Z-(3,4,5-triacetoxyben- IR(KBr)ν(cm$^{-1}$): 1790, 1670, 1375, 1330, 1185

NMR(CDCl$_3$)δ(ppm): 2.13, 2.28 (9H, s, 3xOAc) 3.60 (2H, br s, 2-CH$_3$) 5.08 (2H, s, CH$_2$CO$_2$) 6.90, 7.00 (2H, each s, Ph$_2$CH) 7.27, 7.35 (20H, each s, PhHD 2CH) 7.57 (1H, s, Oxazole 5-CH) 7.82 (2H, s, Aromatic ring CH) (3) To 2.38 g of the compound obtained in Example 10-(2), 1 ml of anisole and 5 ml of trifluoroacetic acid were added, and the mixture was stirred at room temperature for 30 minutes. To the reaction solution, 50 ml of ethyl ether and 20 ml of n-hexane were added, whereby a trifluoroacetate of 7β-[2-(2-aminooxazol-4-yl)-2-Z-(3,4,5-triacetoxybenzoyloxyimino)acetamido]-3-(1-carboxymethyl-1H-tetrazol-5-yl)thiomethyl-3-cephem-4-carboxylic acid precipitated. The precitates were collected by filtration.

Yield: 1.77 g

IR(KBr)ν(cm$^{-1}$): 1790, 1740, 1440, 1380, 1330, 1190

NMR[(CD$_3$)$_2$CO]δ(ppm): 2.30 (9H, s, 3xOAc) 3.68 (2H, br s, 2-CH$_3$) 6.80 (2H, s, Tetrazole 1-CH$_2$COO) 7.68 (1H, s, Oxazole 5-CH) 7.87 (2H, s, Aromatic ring CH)

In water, 1.69 g of the above trifluoroacetate was suspended, and 7.36 ml of a 0.5N sodium hydrogen-carbonate aqueous solution was gradually added. A small amount of insoluble matters were removed by filtration, and the filtrate was subjected to Amberlite XAD-2 column chromatography. The eluate with ethanol:water=4:1, was collected, concentrated under reduced pressure and freeze-dried, whereby 1.15 g of a sodium salt of 7β-[2-(2-aminooxazol-4-yl)-2-Z-(3,4,5-triacetoxybenzoyloxyimino)acetamido]-3-(1-carboxymethyl-1H-tetrazol-5-yl)thiomethyl-3-cephem-4-carboxylic acid was obtained.

We claim:

1. A cephalosporin compound having the formula:

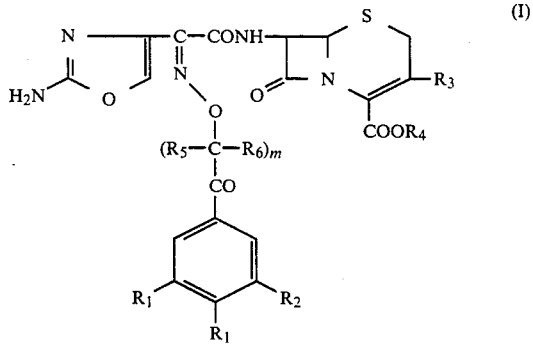

wherein R$_1$ is a hydroxy group, a lower alkanoyloxy group or a lower alkoxycarbonyl group, R$_2$ is a hydrogen atom, a hydroxy group, a lower alkanoyloxy group or a lower alkoxycarbonyloxy group, R$_3$ is a hydrogen atom, a halogen atom, a lower alkyl group, a lower alkenyl group, a lower alkoxy group, or —CH$_2$R$_7$ wherein R$_7$ is a hydrogen atom, an azido group, a lower alkanoyloxy group, a carbamoyloxy group, a pyridinium group, a 4-sulfoethyl pyridinium group, or a thiazolylthio, thiadiazolylthio, triazolylthio, oxazolylthio, tetrazolylthio, pyridinylthio, pyrimidinylthio or triazinylthio group which is unsubstituted or substituted by a lower alkyl, carboxyalkyl or dimethylaminoethyl group, R$_4$ is a hydrogen atom or a carboxy-protecting group, each of R$_5$ and R$_6$ is a hydrogen atom or a lower alkyl group, or R$_5$ and R$_6$ form a cycloalkylidene group together with the carbon atom to which they are attached, and m is 0 or 1, or a pharmaceutically acceptable salt thereof.

2. The cephalosporin compound or the pharmaceutically acceptable salt thereof according to claim 1, wherein R$_2$ is a hydrogen atom or a lower alkanoyloxy group, R$_3$ is —CH$_2$R$_7$ wherein R$_7$ is a lower alkanoyloxy group or a thaizolylthio, thiadiazolylthio, triazolylthio, oxazolylthio, tetrazolylthio, pyridinylthio, pyrimidinylthio or trizinylthio group which is unsubstituted or substituted by a lower alkyl, carboxyalkyl or dimethylaminoethyl group, each of R$_5$ and R$_6$ is a hydrogen atom, and m is 1.

3. The cephalosporin compound or the pharmaceutically acceptable salt thereof according to claim 1, wherein R$_2$ is a hydrogen atom or a lower alkanoyloxy group, R$_3$ is —CH$_2$R$_7$ wherein R$_7$ is a lower alkanoyloxy group or a thiazolylthio, thiadiazolylthio, triazolylthio, oxazolylthio, tetrazolylthio, pyridinylthio, pyrimidinylthio or triazinylthio group which is unsubstituted or substituted by a lower alkyl, carboxyalkyl or dimethylaminoethyl group, and m is 0.

4. 7β-[2-(2-aminooxazol-4-yl)-2-Z-(3,4-diacetoxybenzoyloxyimino)acetamido]cephalosporanic acid or a pharmaceutically acceptable salt thereof, according to claim 1.

5. 7β-[2-(2-aminooxazol-4-yl)-2-Z-(3,4-diacetoxybenzoyloxyimino)acetamido]-3-(1-methyl-1H-tetrazol-5-yl)thiomethyl-3-cephem-4-carboxylic acid or a pharmaceutically acceptable salt thereof, according to claim 1.

6. 7β-[2-(2-aminooxazol-4-yl)-2-Z-(3,4-diacetoxybenzoyloxyimino)acetamido]-3-(2-methyl-1,3,4-thiadiazol-5-yl)thiomethyl-3-cephem-4-carboxylic acid or a pharmaceutically acceptable salt thereof, according to claim 1.

7. 7β-[2-(2-aminooxazol-4-yl)-2-Z-(3,4-diacetoxybenzoyloxyimino)acetamido]-3-(1-carboxymethyl-1H-tetrazol-5-yl)thiomethyl-3-cephem-4-carboxylic acid or a pharmaceutically acceptable salt thereof, according to claim 1.

8. 7β-[2-(2-aminooxazol-4-yl)-2-Z-(3,4,5-triacetoxybenzoyloxyimino)acetamido]-3-(1-methyl-1H-tetrazol-5-yl)-thiomethyl-3-cephem-4-carboxylic acid or a pharmaceutically acceptable salt thereof, according to claim 1.

9. 7β-[2-(2-aminooxazol-4-yl)-2-Z-(3,4-diethoxycarbonyloxybenzoyloxyimino)acetamido]-3-(1-methyl-1H-tetrazol-5-yl)-thiomethyl-3-cephem-4-carboxylic acid or a pharmaceutically acceptable salt thereof, according to claim 1.

10. 7β-[2-(2-aminooxazol-4-yl)-2-Z-(3,4,5-triacetoxybenzoyloxyimino)acetamido]-3-(1-carboxymethyl-1H-tetrazol-5-yl)thiomethyl-3-cephem-4-carboxylic acid or a pharmaceutically acceptable salt thereof, according to claim 1.

* * * * *